(12) United States Patent
Jiang et al.

(10) Patent No.: US 7,677,797 B2
(45) Date of Patent: Mar. 16, 2010

(54) X-RAY IMAGING STAND AND X-RAY IMAGING APPARATUS

(75) Inventors: Lin Jiang, Beijing (CN); Xinyu Yan, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/249,559

(22) Filed: Oct. 10, 2008

(65) Prior Publication Data
US 2009/0097618 A1  Apr. 16, 2009

(30) Foreign Application Priority Data
Oct. 12, 2007  (CN) ............ 200710180775

(51) Int. Cl.
*H01J 31/49* (2006.01)
(52) U.S. Cl. .................... 378/189; 378/208
(58) Field of Classification Search ............ 378/20, 378/62, 189, 193–198, 204, 208
See application file for complete search history.

(56) References Cited

U.S. PATENT DOCUMENTS

| 4,365,344 | A | 12/1982 | Dornheim |
| 4,468,803 | A | 8/1984 | Ronci |
| 5,666,392 | A | 9/1997 | Ploetz |
| 6,155,713 | A | 12/2000 | Watanabe |
| 6,309,102 | B1 | 10/2001 | Stenfors |
| 6,851,851 | B2 | 2/2005 | Smith et al. |
| 6,851,853 | B2 | 2/2005 | Nakagawa et al. |
| 7,180,978 | B2 | 2/2007 | McKenna |
| 2006/0165212 | A1 | 7/2006 | Sasaki et al. |
| 2006/0210021 | A1* | 9/2006 | Matsumoto et al. ......... 378/196 |
| 2007/0147588 | A1 | 6/2007 | Noda et al. |
| 2007/0253539 | A1 | 11/2007 | Noda et al. |
| 2008/0159486 | A1 | 7/2008 | Hesl et al. |
| 2009/0092223 | A1* | 4/2009 | Kobayashi .................. 378/10 |

FOREIGN PATENT DOCUMENTS

JP   11-155850   6/1999

\* cited by examiner

*Primary Examiner*—Courtney Thomas
(74) *Attorney, Agent, or Firm*—Armstrong Teasdale LLP (57) ABSTRACT

An X-ray imaging stand that supports an upright X-ray imaging panel by a column standing vertically through a carriage, includes a bar-like member having a longitudinal bar section that extends from the carriage in the upward direction over the upper end of the X-ray imaging panel and a horizontal bar section that extends from the leading end of the longitudinal bar section in the horizontal direction over the surface of the X-ray imaging panel receiving the X-ray, and a support mechanism that supports the longitudinal bar section of the bar-like member above the carriage such that the angle thereof is variable in plural stages in a plane parallel to the surface of the X-ray imaging panel receiving the X-ray.

20 Claims, 7 Drawing Sheets

X-RAY IMAGING STAND AND X-RAY IMAGING APPARATUS

CROSS REFERENCE TO RELATED APPLICATIONS

This application claims the benefit of Chinese Patent Application No. 20071018775.1 filed Oct. 12, 2007, which is hereby incorporated by reference in its entirety.

BACKGROUND OF THE INVENTION

The subject matter described herein relates to an X-ray imaging stand and an X-ray imaging apparatus, and more particularly, to an X-ray imaging stand that supports a vertically-arranged X-ray imaging panel by a column standing vertically, and an X-ray imaging apparatus having the X-ray stand.

An X-ray imaging apparatus irradiates an X-ray to a patient from an X-ray irradiator, and receives the transmitted X-ray by an X-ray imaging panel so as to form a fluoroscopic image. There are X-ray imaging apparatuses using an X-ray stand. The X-ray stand supports a vertically-arranged X-ray imaging panel by a vertical column (e.g., see Japanese Unexamined Patent Publication No. Hei 11(1999)-155850).

When a fluoroscopic image of a breast is imaged from the side, a patient faces the X-ray imaging panel sideways with both arms raised. In order to facilitate the posture with both arms raised, a grip bar is provided to the X-ray imaging stand. The grip bar is composed of a longitudinal bar section rising from a carriage of the X-ray imaging panel and a horizontal bar section that becomes horizontal above the head of the patient. The patient grips the horizontal bar section with both hands to keep raising both hands.

The comfortable direction of raising hands for the patient is not limited to the right upward direction, but is mostly a direction slightly forward from the right upward direction. The degree of the direction slightly forward from the right upward direction varies depending upon a patient, and is exactly opposite depending upon whether the patient faces to the right or to the left.

BRIEF DESCRIPTION OF THE INVENTION

Accordingly, the subject of the invention is to realize an X-ray imaging stand in which the grip bar can minutely be adjusted, and an X-ray imaging apparatus having the X-ray imaging stand.

According to one aspect, the invention is an X-ray imaging stand that supports an upright X-ray imaging panel by a column standing vertically through a carriage, the X-ray imaging stand including a bar-like member having a longitudinal bar section that extends from the carriage in the upward direction over the upper end of the X-ray imaging panel and a horizontal bar section that extends from the leading end of the longitudinal bar section in the horizontal direction over the surface of the X-ray imaging panel receiving the X-ray, and a support mechanism that supports the longitudinal bar section of the bar-like member above the carriage such that the angle thereof is variable in plural stages in a plane parallel to the surface of the X-ray imaging panel receiving the X-ray.

According to the second aspect, the invention is the X-ray imaging stand, described in the first aspect, wherein the support mechanism has a rotating member that includes plural notches corresponding to the angles in plural stages of the longitudinal bar section and rotates with the rotation of the longitudinal bar section in the direction for changing the angle, a preventing member that engages with the rotating member to prevent its rotation, and a switching mechanism that moves with the pivot of the longitudinal bar section in the direction vertical to the direction for changing the angle so as to make a changeover of an engagement and non-engagement between the rotating member and the preventing member.

According to the third aspect, the invention is the X-ray imaging stand, described in the second aspect, wherein the rotating member is a sector gear, and the preventing member is a rack.

According to the fourth aspect, the invention is the X-ray imaging stand, described in the third aspect, wherein the switching mechanism makes a changeover of the engagement and non-engagement between the sector gear and the rack by the pivot of a rotational shaft of the sector gear that moves with the pivot of the longitudinal bar section.

According to the fifth aspect, the invention is the X-ray imaging stand, described in the fourth aspect, wherein the pivot is made with one end of the rotational shaft as a center.

According to the sixth aspect, the invention is the X-ray imaging stand, described in the fifth aspect, wherein the one end of the rotational shaft is supported by a block that can be rotated about a horizontal shaft.

According to the seventh aspect, the invention is the X-ray imaging stand, described in the fifth or sixth aspect, wherein the rotational shaft has a returning spring mounted to the other side.

According to the eighth aspect, the invention is the X-ray imaging stand, described in the seventh aspect, wherein the spring is a coil spring.

According to the ninth aspect, the invention is the X-ray imaging stand, described in the second aspect, wherein the rotating member has an attachment section for the longitudinal bar section.

According to the tenth aspect, the invention is the X-ray imaging stand, described in the ninth aspect, wherein the attachment section is a cylindrical member into which the longitudinal bar section is fitted.

According to the eleventh aspect, the invention is an X-ray imaging apparatus including an X-ray imaging stand that supports a upright X-ray imaging panel by a column standing vertically through a carriage, and an X-ray irradiator, the X-ray imaging apparatus including a bar-like member having a longitudinal bar section that extends from the carriage in the upward direction over the upper end of the X-ray imaging panel and a horizontal bar section that extends from the leading end of the longitudinal bar section in the horizontal direction over the surface of the X-ray imaging panel receiving the X-ray, and a support mechanism that supports the longitudinal bar section of the bar-like member above the carriage such that the angle thereof is variable in plural stages in a plane parallel to the surface of the X-ray imaging panel receiving the X-ray.

According to the twelfth aspect, the invention is the X-ray imaging apparatus, described in the eleventh aspect, wherein the support mechanism has a rotating member that includes plural notches corresponding to the angles in plural stages of the longitudinal bar section and rotates with the rotation of the longitudinal bar section in the direction for changing the angle, a preventing member that engages with the rotating member to prevent its rotation, and a switching mechanism that moves with the pivot of the longitudinal bar section in the direction vertical to the direction for changing the angle so as to make a changeover of an engagement and non-engagement between the rotating member and the preventing member.

According to the thirteenth aspect, the invention is the X-ray imaging apparatus, described in the twelfth aspect, wherein the rotating member is a sector gear, and the preventing member is a rack.

According to the fourteenth aspect, the invention is the X-ray imaging apparatus, described in the thirteenth aspect, wherein the switching mechanism makes a changeover of the engagement and non-engagement between the sector gear and the rack by the pivot of a rotational shaft of the sector gear that moves with the pivot of the longitudinal bar section.

According to the fifteenth aspect, the invention is the X-ray imaging apparatus, described in the fourteenth aspect, wherein the pivot is made with one end of the rotational shaft as a center.

According to the sixteenth aspect, the invention is the X-ray imaging apparatus, described in the fifteenth aspect, wherein the one end of the rotational shaft is supported by a block that can be rotated about a horizontal shaft.

According to the seventeenth aspect, the invention is the X-ray imaging apparatus, described in the fifteenth or sixteenth aspect, wherein the rotational shaft has a returning spring mounted to the other side.

According to the eighteenth aspect, the invention is the X-ray imaging apparatus, described in the seventeenth aspect, wherein the spring is a coil spring.

According to the nineteenth aspect, the invention is the X-ray imaging apparatus, described in the twelfth aspect, wherein the rotating member has an attachment section for the longitudinal bar section.

According to the twentieth aspect, the invention is the X-ray imaging apparatus, described in the nineteenth aspect, wherein the attachment section is a cylindrical member into which the longitudinal bar section is fitted.

According to one aspect, the X-ray imaging stand that supports an upright X-ray imaging panel by a column standing vertically through a carriage, includes a bar-like member having a longitudinal bar section that extends from the carriage in the upward direction over the upper end of the X-ray imaging panel and a horizontal bar section that extends from the leading end of the longitudinal bar section in the horizontal direction over the surface of the X-ray imaging panel receiving the X-ray, and a support mechanism that supports the longitudinal bar section of the bar-like member above the carriage such that the angle thereof is variable in plural stages in a plane parallel to the surface of the X-ray imaging panel receiving the X-ray, whereby the invention can realize the X-ray imaging stand in which the grip bar can minutely be adjusted.

According to the eleventh aspect, the X-ray imaging apparatus including an X-ray imaging stand that supports an upright X-ray imaging panel by a column standing vertically through a carriage, and an X-ray irradiator, includes a bar-like member having a longitudinal bar section that extends from the carriage in the upward direction over the upper end of the X-ray imaging panel and a horizontal bar section that extends from the leading end of the longitudinal bar section in the horizontal direction over the surface of the X-ray imaging panel receiving the X-ray, and a support mechanism that supports the longitudinal bar section of the bar-like member above the carriage such that the angle thereof is variable in plural stages in a plane parallel to the surface of the X-ray imaging panel receiving the X-ray. Therefore, the invention can realize an X-ray imaging apparatus having an X-ray imaging stand in which the grip bar can minutely be adjusted.

According to the second or twelfth aspect, the support mechanism has a rotating member that includes plural notches corresponding to the angles in plural stages of the longitudinal bar section and rotates with the rotation of the longitudinal bar section in the direction for changing the angle, a preventing member that engages with the rotating member to prevent its rotation, and a switching mechanism that moves with the pivot of the longitudinal bar section in the direction vertical to the direction for changing the angle so as to make a changeover of an engagement and non-engagement between the rotating member and the preventing member, whereby the angle of the longitudinal bar section can easily be adjusted and can easily be retained.

According to the third or thirteenth aspect, the rotating member is a sector gear, and the preventing member is a rack, whereby the adjustment of the angle in plural stages is easily performed.

According to the fourth or fourteenth aspect, the switching mechanism makes a changeover of the engagement and non-engagement between the sector gear and the rack by the pivot of a rotational shaft of the sector gear that moves with the pivot of the longitudinal bar section, whereby the configuration is simplified.

According to the fifth or fifteenth aspect, the pivot is made with one end of the rotational shaft as a center, whereby the changeover of the engagement and non-engagement between the sector gear and the rack is facilitated.

According to the sixth or sixteenth aspect, the one end of the rotational shaft is supported by a block that can be rotated about a horizontal shaft, whereby the pivot is easily made.

According to the seventh or seventeenth aspect, the rotational shaft has a returning spring mounted to the other side, whereby the pivot is easily returned.

According to the eighth or eighteenth aspect, the spring is a coil spring, whereby the configuration is simplified.

According to the ninth or nineteenth aspect, the rotating member has an attachment section for the longitudinal bar section, whereby the integration with the longitudinal bar section is facilitated.

According to the tenth or twentieth aspect, the attachment section is a cylindrical member into which the longitudinal bar section is fitted, whereby the longitudinal section is easily attached or detached.

Further object and advantages of the present invention will be apparent from the following description of the preferred embodiments of the invention as illustrated in the accompanying drawings.

DETAILED DESCRIPTION OF THE INVENTION

Figure 1:
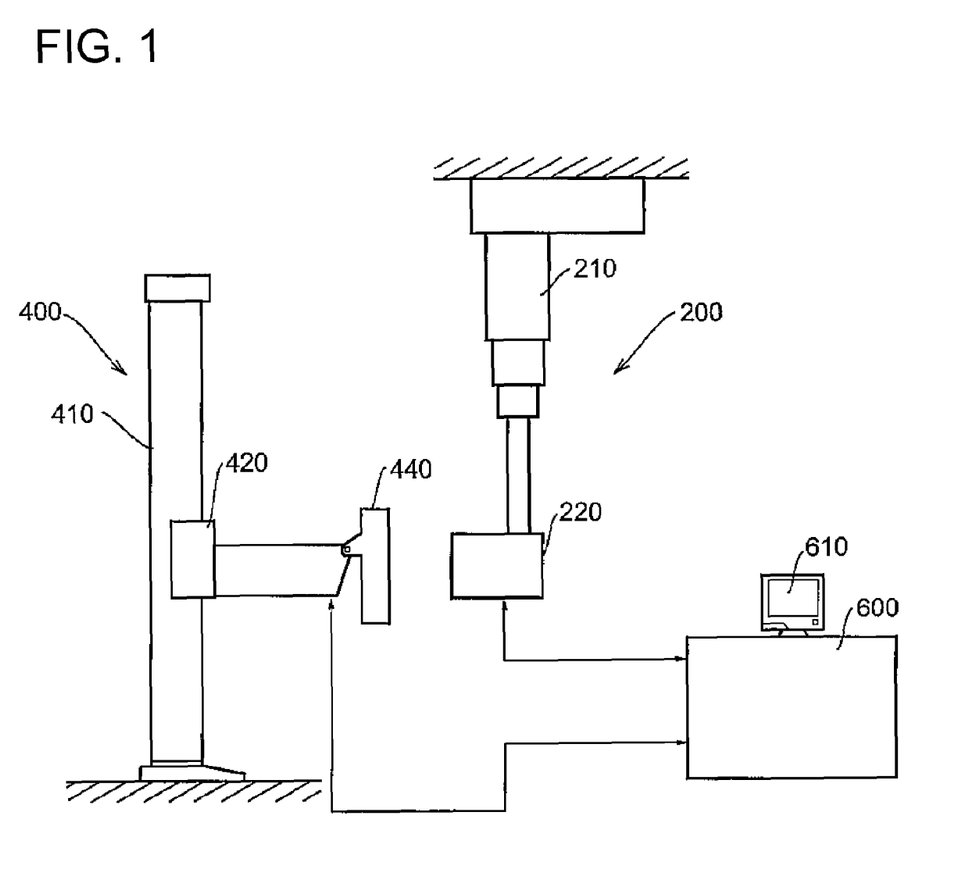
FIG. 1 is a view showing a configuration of an X-ray imaging apparatus.

Various embodiments of the invention will be explained in detail with reference to the drawings. The invention is not limited to the embodiments described herein. FIG. 1 schematically shows the configuration of an X-ray imaging apparatus.

As shown in FIG. 1, the present apparatus includes an X-ray irradiating device 200 and an X-ray imaging stand 400. The X-ray irradiating device 200 is configured such that an X-ray irradiator 220 is attached at the leading end of a column 210 hanging from a ceiling. The X-ray irradiator 220 can change its direction so as to change the irradiation direction of the X-ray. The column 210 supporting the X-ray irradiator 220 is extendable and retractable in the longitudinal direction, and movable in the horizontal direction along the ceiling. The X-ray irradiator 220 is one example of an X-ray irradiator in the invention.

The X-ray imaging stand 400 is configured such that a carriage 420 is attached to a column 410, which stands upright on the floor, so as to be capable of moving up and down, and an X-ray imaging panel 440 is attached to the leading end of an arm of the carriage 420.

The column 410 is one example of a column in the invention. The carriage 420 is one example of a carriage in the invention. The X-ray imaging panel 440 is one example of an X-ray imaging panel in the invention.

The X-ray imaging panel 440 has a plate-like structure, wherein the direction thereof is changeable in order that the X-ray incident surface becomes vertical or horizontal according to the incident direction of the X-ray. The X-ray imaging panel 440 has a two-dimensional array of an X-ray detecting device incorporated therein.

The detection signal of the X-ray imaging panel 440 is inputted to an operator console 600. The operator console 600 reconstructs the fluoroscopic image, which is a subject to be imaged, on the basis of the input signal from the X-ray imaging panel 440, and displays the reconstructed image on a display 610.

The X-ray imaging panel 440 may hold an X-ray film cassette, instead of the two-dimensional array of the X-ray detecting device. When the X-ray film cassette is used, the fluoroscopic image is made visible by a developing process.

The operator console 600 controls the X-ray irradiating device 200 and the X-ray imaging stand 400 under the operation by an operator. The operator console 600 controls the position of the X-ray irradiator 220 of the X-ray irradiating device 200 in the horizontal and vertical direction, and further controls the X-ray intensity and irradiation timing thereof. The operator console 600 controls the height of the X-ray imaging panel 440 of the X-ray imaging stand 400 according to the X-ray irradiator 220, and further controls its posture so as to become vertical or horizontal according to the X-ray incident direction.

Figure 2:
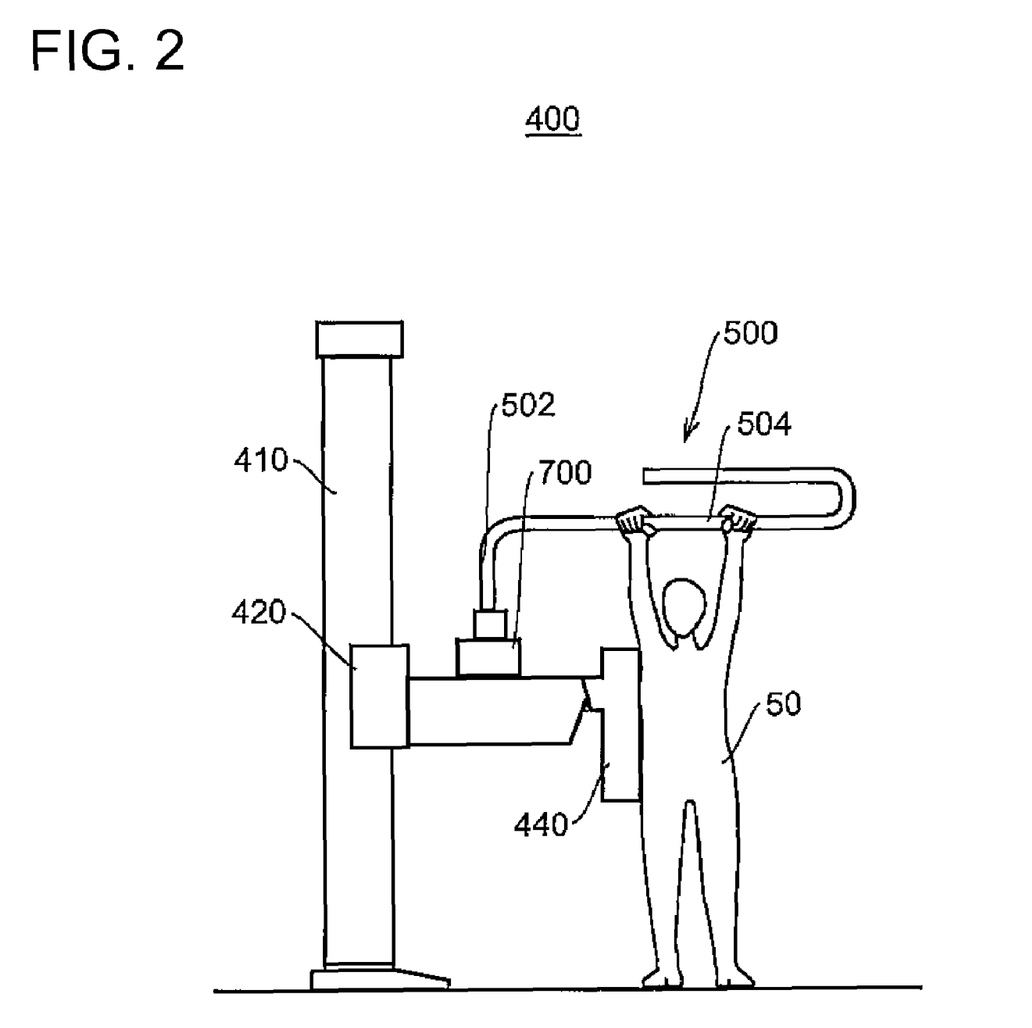
FIG. 2 is a view showing a configuration of an X-ray imaging stand that may be used with the X-ray imaging apparatus shown in FIG. 1.

FIG. 2 is a view showing a state in which a fluoroscopic image of a breast is imaged from the side at the X-ray imaging stand 400. As shown in FIG. 2, the X-ray imaging panel 440 is vertically supported by the carriage 420, and a patient 50 grips a grip bar 500 with both hands so as to face the X-ray imaging panel 440 from the side with both hands raising.

The grip bar 500 is supported by a support mechanism 700 above the carriage 420. The grip bar 500 is composed of a longitudinal bar section 502 rising from the support mechanism 700 and a horizontal bar section 504 extending from its leading end to the position above the head of the patient 50 in the horizontal direction. The patient 50 grips the horizontal bar section 504 with both hands so as to keep raising his/her hands.

The grip bar 500 is one example of a bar-like member in the invention. The longitudinal bar section 502 is one example of a longitudinal bar section in the invention. The horizontal bar section 504 is one example of a horizontal bar section in the invention. The support mechanism 700 is one example of a support mechanism in the invention.

Figure 3:
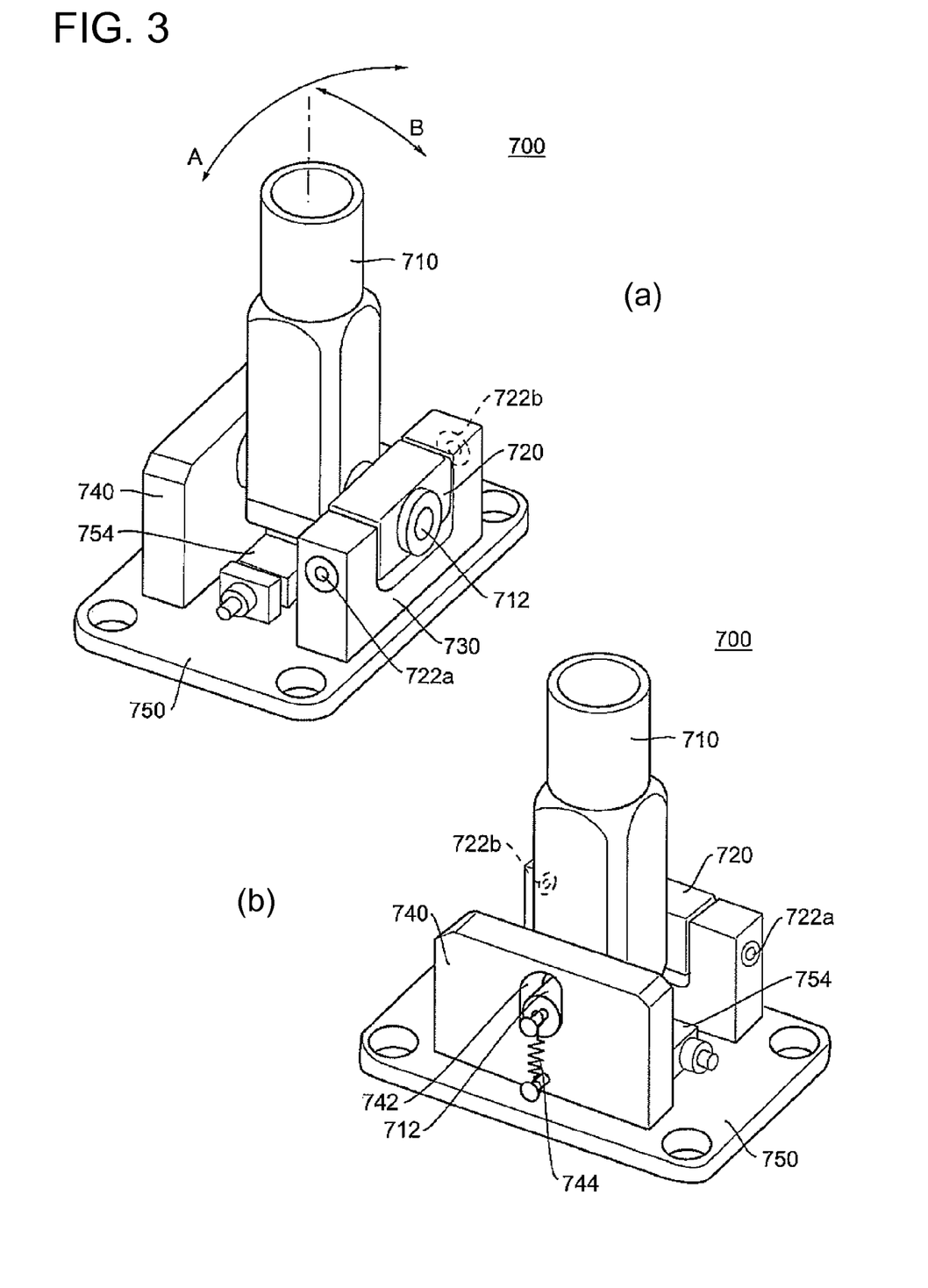
FIGS. 3(a) and 3(b) are views showing a configuration of a support mechanism of a grip bar.

FIGS. 3(a) and 3(b) show the configuration of the support mechanism 700. FIGS. 3(a) and 3(b) are perspective views showing the support mechanism 700 viewed from various angles. As shown in FIGS. 3(a) and 3(b), the support mechanism 700 has a cylindrical member 710. The opening of the cylindrical member 710 is directed upward.

The longitudinal bar section 502 of the grip bar 500 is fitted into the cylindrical member 710 from the opening end. Thus, the cylindrical member 710 is integrated with the grip bar 500. The cylindrical member 710 is one example of an attachment section in the invention. The cylindrical member 710 is also one example of a cylindrical member in the invention.

The end portion of the cylindrical member 710 that is opposite to the opening end is supported by a lateral shaft 712. The lateral shaft 712 is orthogonal to the shaft direction of the cylindrical member 710. One end of the lateral shaft 712 is supported by a rectangle block 720. The support of the cylindrical member 710 by the lateral shaft 712 or the support of the lateral shaft 712 by the rectangular block 720 is carried out through a bearing.

Therefore, the cylindrical member 710 is rotatable about the lateral shaft 712. The rotatable direction is indicated by an arrow A. It is to be noted that the rotation in this direction is always prevented by a preventing mechanism, and the rotation is possible only when the prevention is released. The preventing mechanism will be described later.

The rectangular block 720 is supported by a pair of horizontal shafts 722a and 722b provided at its both ends. The horizontal shafts 722a and 722b are orthogonal to the lateral shaft 712. The horizontal shafts 722a and 722b are supported by a U-shaped block 730. The U-shaped block 730 is fixed to a base 750 in a state of standing upright. The support of the rectangular block 720 by the horizontal shafts 722a and 722b and the support of the horizontal shafts 722a and 722b by the U-shaped block 730 are carried out through a bearing.

The other end of the lateral shaft 712 is supported by an elongated block 740. The elongated block 740 is fixed to the base 750 in a state of standing upright so as to be parallel to the U-shaped block 730. The elongated block 740 has an elongated hole 742. The elongated hole 742 is a lengthwise hole.

The lateral shaft 712 is supported such that the other end thereof penetrates the elongated hole 742 to expose to the outside. Force of a spring 744 is applied downward to the exposed end. A coil spring is used as the spring 744, for example.

The portion composed of the cylindrical member 710, lateral shaft 712 and rectangular block 720 is pivotable about the horizontal shafts 722a and 722b within the range allowed by the elongated hole 742. The pivotable direction is indicated by an arrow B. The pivot of the portion composed of the cylindrical member 710, lateral shaft 712 and rectangular block 720 is simply referred to as the pivot of the cylindrical member 710 below.

The prevention by the later-described preventing mechanism is released by the pivot movement of the cylindrical member 710 in the direction in which the cylindrical member 710 tilts. The prevention by the later-described preventing mechanism is recovered by the pivot movement of the cylindrical member 710 in the direction in which the cylindrical member 710 returns to the upright state. The portion composed of the cylindrical member 710, lateral shaft 712, rectangular block 720 and horizontal shafts 722a and 722b is one example of a switching mechanism in the invention.

Figure 4:
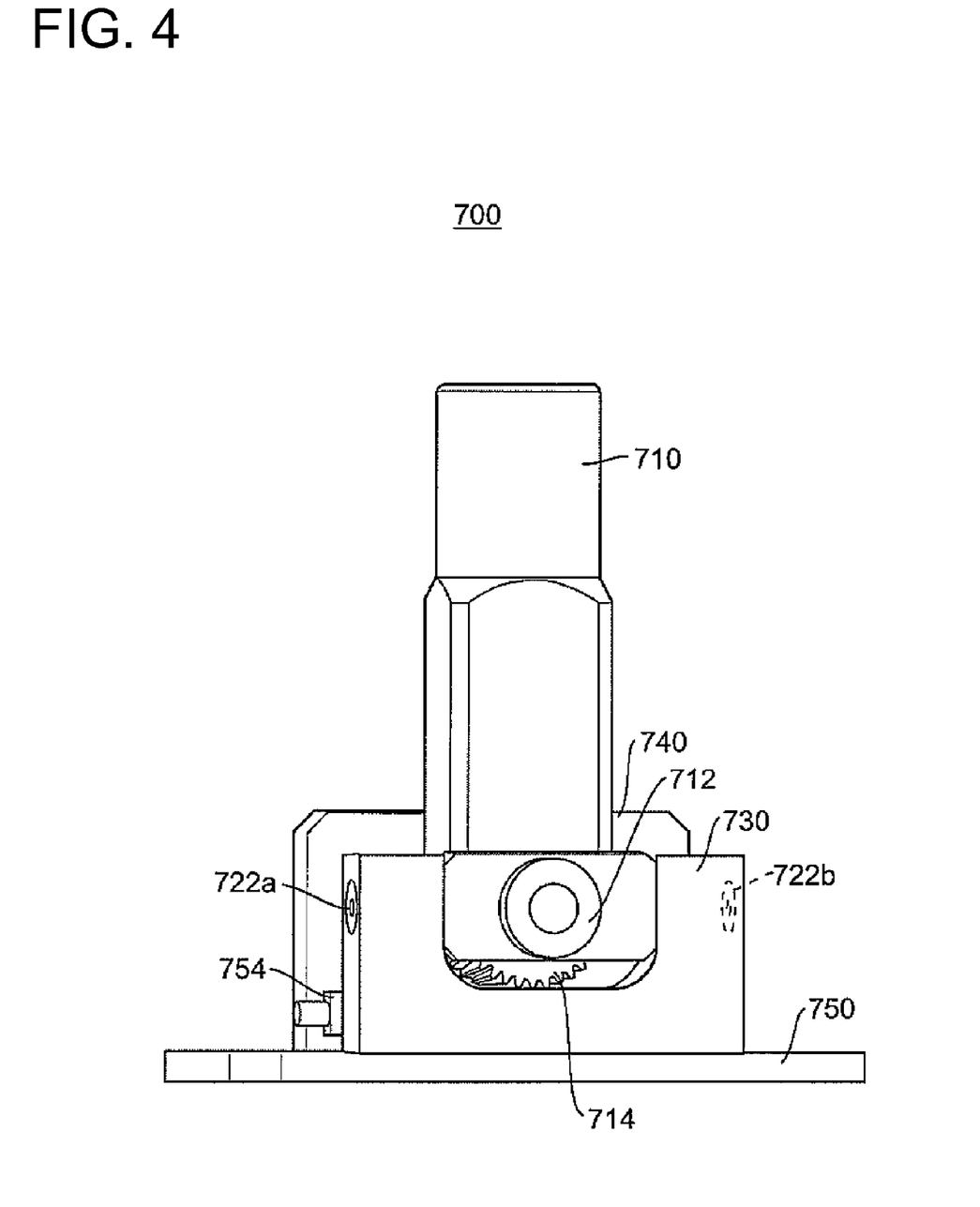
FIG. 4 is a view showing a configuration of a support mechanism of a grip bar.

FIG. 4 shows a state in which the support mechanism 700 is viewed from another angle. FIG. 4 shows the support mechanism 700 viewed from the angle that is slightly shifted to the left from the angle facing the U-shaped block 730.

As shown in FIG. 4, the cylindrical member 710 has a sector gear 714 at the lowermost part. The lateral shaft 712 is defined as the center shaft of the sector gear 714, and the sector gear 714 is integrated with the cylindrical member 710. As shown in FIGS. 3(a), 3(b), and 4, a rack 754 is provided to the base 750 so as to correspond to the sector gear 714. The rack 754 is fixed on the base 750 between the U-shaped block 730 and the elongated block 740 so as to face the sector gear 714.

The sector gear 714 forms the preventing mechanism together with the rack 754. The sector gear 714 is one example of a rotating member in the invention. Plural teeth of the sector gear 714 form plural notches of the rotating member. The sector gear 714 is also one example of a sector gear in the invention. The rack 754 is one example of a preventing member in the invention. The rack 754 is also one example of a rack in the invention.

Figure 5:
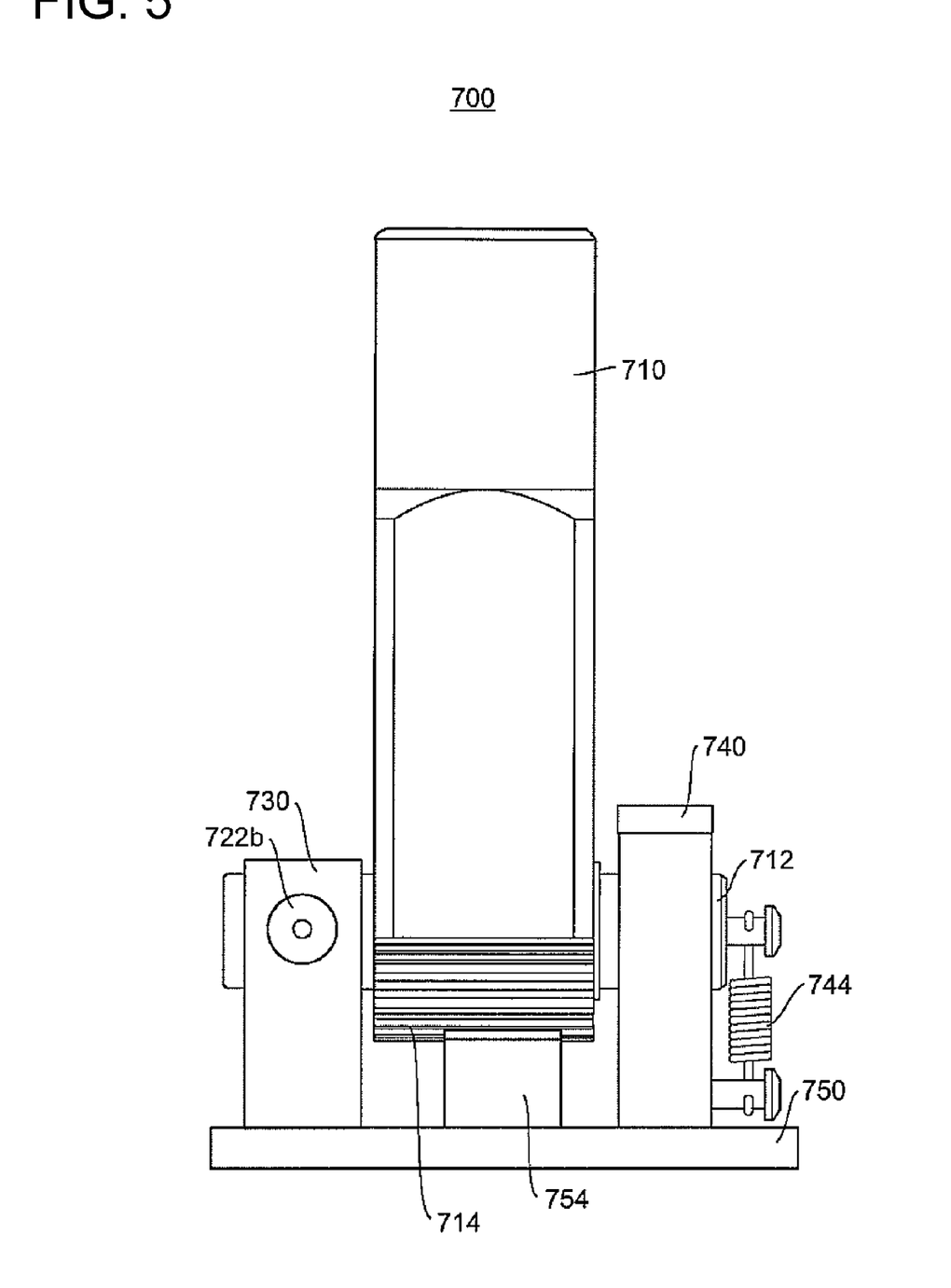
FIG. 5 is a view showing the operation of the support mechanism of the grip bar.

FIG. 5 shows a relationship between the sector gear 714 and the rack 754. FIG. 5 is a view showing the configuration shown in FIG. 4 from the right side. In FIG. 5, the cylindrical member 710 is in its upright state. In this case, the lateral shaft 712 becomes horizontal, and the sector gear 714 is geared with the rack 754. Therefore, the rotation with the lateral shaft 712 as a center is prevented. The meshing between the sector gear 714 and the rack 754 is referred to as engagement in the present specification.

Figure 6:
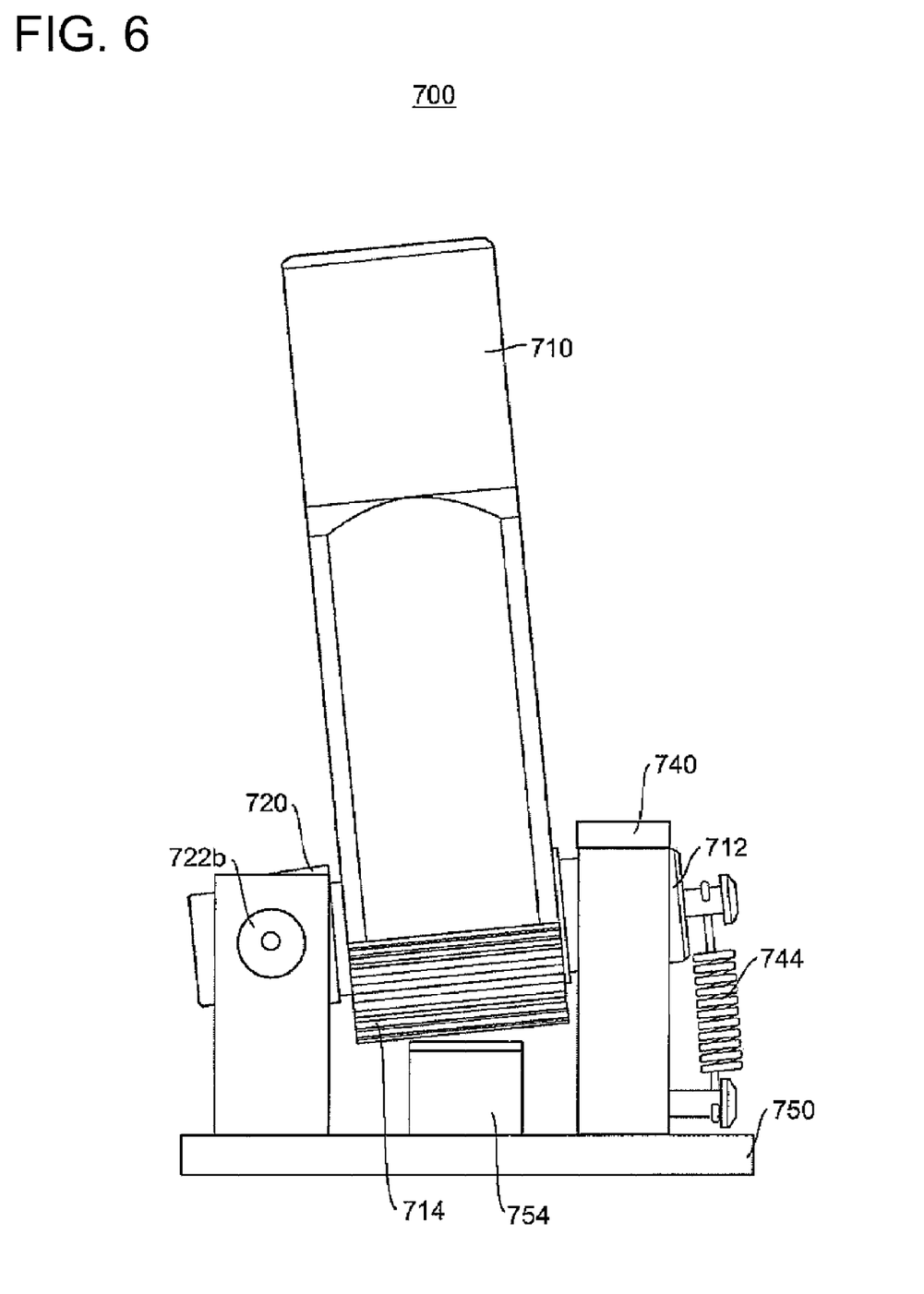
FIG. 6 is a view showing the operation of the support mechanism of the grip bar.

The meshing between the sector gear 714 and the rack 754 can be released by tilting the cylindrical member 710 to the left about the horizontal shafts 722a and 722b as shown in FIG. 6. The meshing between the sector gear 714 and the rack 754 is released, whereby the cylindrical member 710 becomes rotatable about the lateral shaft 712. The release of the meshing between the sector gear 714 and the rack 754 is referred to as non-engagement in the present specification.

When the cylindrical member 710 is rotated at a predetermined angle in the non-engagement state, and then returned to the engagement state, the rotation angle of the cylindrical member 710 about the lateral shaft 712 is fixed to a desired angle. The minimum step for changing the angle is determined by the pitch of the sector gear 714, and the stage for changing the angle is determined by the number of teeth of the sector gear 714. Accordingly, the changing of the angle in the plural stages becomes capable.

Figure 7:
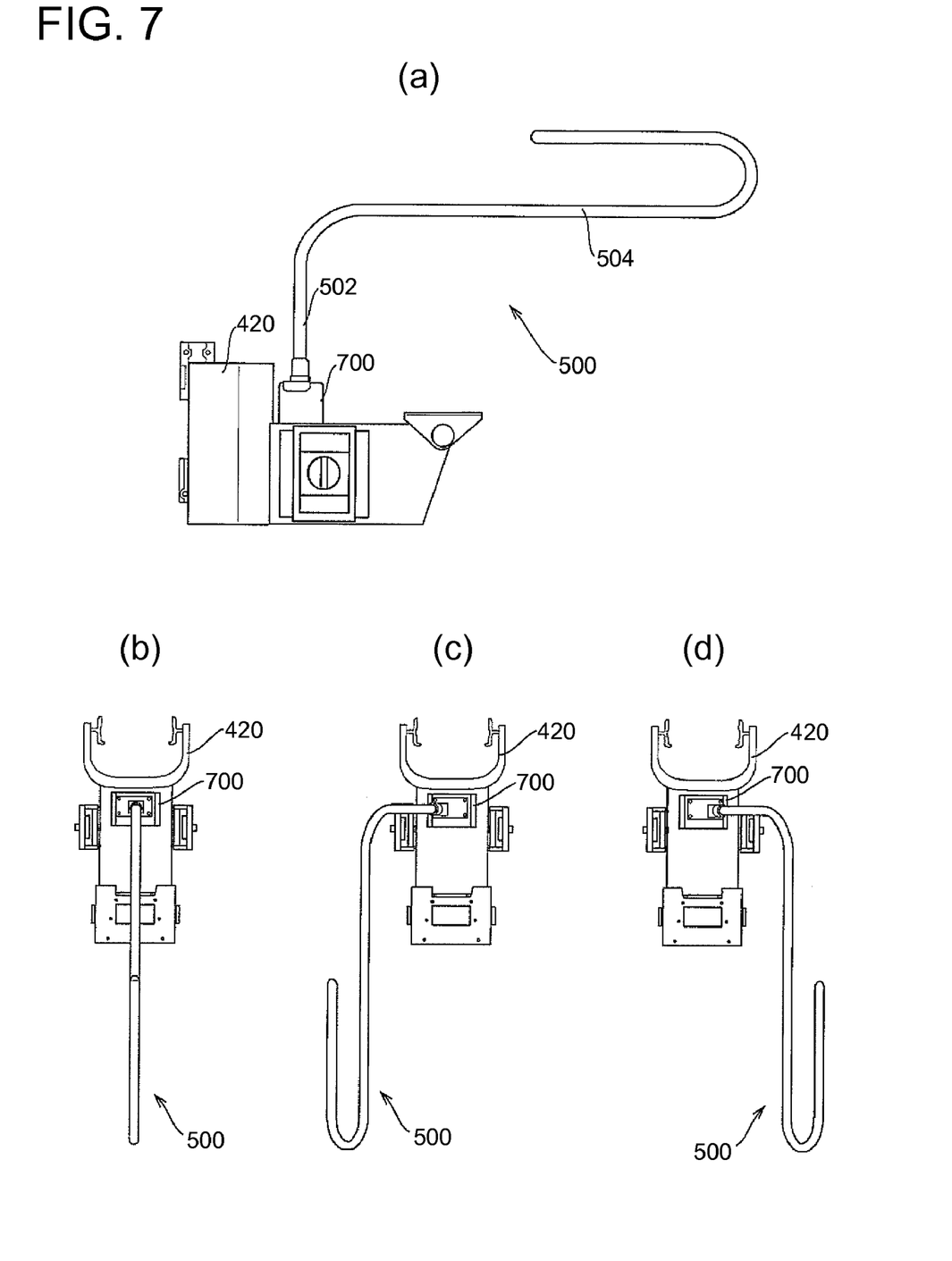
FIGS. 7(a), 7(b), 7(c), and 7(d) are views showing an angular adjustment of the grip bar.

FIGS. 7(a) to 7(d) show an example of adjusting the angle of the grip bar 500. As shown in FIGS. 7a) to 7(d), the grip bar 500 is attached to the carriage 420 above the upper surface of the arm through the support mechanism 700. The lateral shaft 712 of the support mechanism 700 is parallel to the horizontal bar section 504 of the grip bar 500.

FIG. 7(a) is a side view of the carriage, while FIGS. 7(b), (c), and (d) are top views. FIGS. 7(a) and 7(b) show the upright state of the grip bar 500, FIG. 7(c) shows the grip bar 500 rotated to the left, and FIG. 7(d) shows the grip bar 500 rotated to the right.

The angle of the grip bar 500 is adjusted by the following processes. First, the longitudinal bar section 502 of the grip bar 500 is tilted in the direction orthogonal to the angle-adjusting direction. Next, the longitudinal bar section 502 is rotated to the right or to the left by a desired angle with the tilted state. Then the tilt of the longitudinal bar section 502 is returned with the rotated state.

This operation can easily be performed by a doctor, radiographer, or caregiver with one hand. Further, the rotation angle can minutely be adjusted in both right and left directions for every patient. Accordingly, the grip bar 500 can be changed as rotated in the right or in the left by an angle adapting to a patient, and this state can be maintained. The maximum moving range of the horizontal bar section 504 due to the rotation can be set so as to coincide with the width of the X-ray imaging panel 440, for example.

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray imaging stand that supports an upright X-ray imaging panel by a column standing vertically through a carriage, said X-ray imaging stand comprising:
   a bar-like member comprising a longitudinal bar section that extends from said carriage in an upward direction over an upper end of said X-ray imaging panel that is configured to receive an X-ray, and a horizontal bar section that extends from a leading end of said longitudinal bar section in a horizontal direction over a surface of said X-ray imaging panel; and
   a support mechanism adapted to support said longitudinal bar section of said bar-like member above said carriage such that an angle thereof is variable in a plurality of stages in a plane parallel to the surface of said X-ray imaging panel.

2. An X-ray imaging stand according to claim 1, wherein said support mechanism comprises:
   a rotating member comprising a plurality of notches corresponding to the angles in the plurality of stages of said longitudinal bar section, said rotating member configured to rotate according to a rotation of said longitudinal bar section in a direction for changing the angle;
   a preventing member configured to engage said rotating member to prevent rotation of said rotating member; and
   a switching mechanism configured to move according to a pivot of said longitudinal bar section in the direction vertical to the direction for changing the angle in order to make a changeover of an engagement and a non-engagement between said rotating member and said preventing member.

3. An X-ray imaging stand according to claim 2, wherein said rotating member comprises a sector gear, and said preventing member comprises a rack.

4. An X-ray imaging stand according to claim 3, wherein said switching mechanism is configured to make a changeover of the engagement and non-engagement between said sector gear and said rack according to a pivot of a rotational shaft of said sector gear that is configured to move according to the pivot of said longitudinal bar section.

5. An X-ray imaging stand according to claim 4, wherein the pivot is made with a first end of said rotational shaft as a center.

6. An X-ray imaging stand according to claim 5, wherein said first end of said rotational shaft is supported by a block configured to rotate about a horizontal shaft.

7. An X-ray imaging stand according to claim 5, wherein said rotational shaft comprises a returning spring mounted to a second end of said rotational shaft opposite said first end.

8. An X-ray imaging stand according to claim 7, wherein said spring comprises a coil spring.

9. An X-ray imaging stand according to claim 2, wherein said rotating member comprises an attachment section for said longitudinal bar section.

10. An X-ray imaging stand according to claim 9, wherein said attachment section comprises a cylindrical member into which said longitudinal bar section is fitted.

11. An X-ray imaging apparatus comprising:
an X-ray irradiator configured to emit an X-ray;
an upright X-ray imaging panel configured to receive the X-ray; and
an X-ray imaging stand configured to support said X-ray imaging panel by a column standing vertically through a carriage, said X-ray imaging stand comprising:
a bar-like member comprising a longitudinal bar section that extends from said carriage in an upward direction over an upper end of said X-ray imaging panel and a horizontal bar section that extends from a leading end of said longitudinal bar section in a horizontal direction over a surface of said X-ray imaging panel; and
a support mechanism configured to support said longitudinal bar section of said bar-like member above said carriage such that an angle thereof is variable in a plurality of stages in a plane parallel to the surface of said X-ray imaging panel.

12. An X-ray imaging apparatus according to claim 11, wherein said support mechanism comprises:
a rotating member comprising a plurality of notches corresponding to the angles in the plurality of stages of said longitudinal bar section, said rotating member configured to rotate according to a rotation of said longitudinal bar section in a direction for changing the angle;
a preventing member configured to engage said rotating member to prevent rotation of said rotating member; and
a switching mechanism configured to move according to a pivot of said longitudinal bar section in the direction vertical to the direction for changing the angle in order to make a changeover of an engagement and a non-engagement between said rotating member and said preventing member.

13. An X-ray imaging apparatus according to claim 12, wherein said rotating member comprises a sector gear, and said preventing member comprises a rack.

14. An X-ray imaging apparatus according to claim 13, wherein said switching mechanism is configured to make a changeover of the engagement and non-engagement between said sector gear and said rack according to a pivot of a rotational shaft of said sector gear that is configured to move according to the pivot of said longitudinal bar section.

15. An X-ray imaging apparatus according to claim 14, wherein the pivot is made with a first end of said rotational shaft as a center.

16. An X-ray imaging apparatus according to claim 15, wherein said first end of said rotational shaft is supported by a block configured to rotate about a horizontal shaft.

17. An X-ray imaging apparatus according to claim 15, wherein said rotational shaft comprises a returning spring mounted to a second end of said rotational shaft opposite said first end.

18. An X-ray imaging apparatus according to claim 17, wherein said spring comprises a coil spring.

19. An X-ray imaging apparatus according to claim 12, wherein said rotating member comprises an attachment section for said longitudinal bar section.

20. An X-ray imaging apparatus according to claim 19, wherein said attachment section comprises a cylindrical member into which said longitudinal bar section is fitted.

* * * * *